(12) United States Patent
Fujii et al.

(10) Patent No.: US 7,022,502 B2
(45) Date of Patent: Apr. 4, 2006

(54) PROCESS FOR THE BIOLOGICAL PRODUCTION OF L-PIPECOLIC ACID

(75) Inventors: Tadashi Fujii, Fujisawa (JP); Yasuhide Aritoku, Fujisawa (JP); Manabu Mukaihara, Kamakura (JP); Takao Narita, Yatsushiro (JP); Hitosi Agematu, Hadano (JP); Kunio Isshiki, Zama (JP)

(73) Assignee: Mercian Corporation, Tokyo (JP)

( * ) Notice: Subject to any disclaimer, the term of this patent is extended or adjusted under 35 U.S.C. 154(b) by 174 days.

(21) Appl. No.: 10/169,257

(22) PCT Filed: Dec. 22, 2000

(86) PCT No.: PCT/JP00/09137

§ 371 (c)(1),
(2), (4) Date: Jun. 28, 2002

(87) PCT Pub. No.: WO01/48216

PCT Pub. Date: Jul. 5, 2001

(65) Prior Publication Data

US 2003/0207410 A1  Nov. 6, 2003

(30) Foreign Application Priority Data

Dec. 28, 1999  (JP) ............... 11-373389

(51) Int. Cl.
*C12P 17/00* (2006.01)
(52) U.S. Cl. .................... 435/117; 435/117
(58) Field of Classification Search ............ 435/117
See application file for complete search history.

(56) References Cited

FOREIGN PATENT DOCUMENTS

JP       6-38781      2/1994
WO       00/08170     2/2000

OTHER PUBLICATIONS

Tobin et al. Localization of the lysine aminotransferase (lat). . . from *S. clavuliergus* and production of LAT activity in *Escherichia coli*. Bacteriol. (1991) 173(19): 6223-6229.*
Fujii et al. Biotransformation of Lysine to Pipecolate Catalyzed by Lysine 6-Aminotransferase and Pyrroline-5-carboxylate Reductase. Biosci. Biotechnol. Biochem. (2002) 66(3): 622-627.*

Fujii et al. Characterization of Lysine 6-Aminotransferase and Its Structural Gene from *Flavobacterium lutescens* IFO3084. J. Biochem. (Sep., 2000) 128: 391-397.*
Tanizawa et al. L-lysine transaminase from *Flavobacterium lutescens*. Methods in Enzymology (1985) 113: 96-102.*
Steffes et al. J. Bacteriol. (1992) 174(10): 3242-3249.*
Yagi, T., et al. "L-Lysine: 2-Oxoglutarate 6-Aminotransferase. Subunit Structure Composed of Non-Identical Polypeptides and Pyridoxal 5'-Phosphate-Binding Subunit.", J. Biochem. (1980), vol. 87, No. 5, pp. 1395-1402.
Yagi, T., et al. "A Novel Purification Procedure of L-Lysine 6-Aminotransferase From *Flavobacterium Lutescence*.", Biochem. Biophys. Acta (1980), vol. 614, No. 1, pp. 63-70.
Deutch, A.H., et al. "*Escherichia coli* Δ1-pyrroline-5-carboxylatereductase: gene sequence, protein overproduction and purification.", Nucleic Acids Res. (1982), vol. 10, No. 23, pp. 7701-7714.
Steffes, C., et al. "The IysP Gene Encodes the Lysine-Specific Permease.", J. Bacteriol. (1992), vol. 174, No. 10, pp. 3242-3249.
Blattner, F.R., et al. "The Complete Genome Sequence of *Escherichia coli* K-12.", Science (1997), vol. 277, No. 5331, pp. 1453-1474.

(Continued)

*Primary Examiner*—Kathleen M. Kerr
*Assistant Examiner*—Hope Robinson
(74) *Attorney, Agent, or Firm*—Wenderoth, Lind & Ponack L.L.P.

(57) ABSTRACT

A process for the production of L-pipecolic acid which comprises the step of reducing delta-1-piperideine-6-carboxylic acid by the use of pyrroline-5-carboxylate reductase. The delta-1-piperideine-6-carboxylic acid is obtained by the step of converting L-lysine by the use of lysine 6-aminotransferase encoded by a gene of *Flavobacterium lutescens*. The steps of reducing delta-1-piperideine-6-carboxylic acid and the converting of L-lysine into L-pipecolic acid by the use of lysine 6-aminotransferase are carried out by using a bacterium transformed with a gene encoding lysine 6-aminotransferase wherein such bacterium comprises pyrroline-5-carboxylate reductase encoded by a gene of *Escherichia coli* or a coryneform bacterium. A recombinant bacterium which can be used in this production process is also provided. Thus, the present invention can provide an efficient biological process for the production of L-pipecolic acid (or 2-piperidinecarboxylic acid).

3 Claims, 2 Drawing Sheets

OTHER PUBLICATIONS

Pérez-Llarena, F.J., et al. "The pcd Gene Encoding Piperdine 6-Carboxylic Dehydrogenase Involved in Biosynthesis of α-Aminoadipic Acid Is Located in the Cephamycin Cluster of *Streptomyces clavuligerus*.", J. Bacteriol, (1998), vol. 180, No. 17, pp. 4753-4756.

Leitão, A.L., et al. "Inducing Effect of Diamines on Transcription of the Cephamycin C Genes from the lat and pcbAB Promoters in *Nocardia lactamdurans*.", J. Bacteriol. (Apr. 1999), vol. 181, No. 8, pp. 2379-2384.

J-J. R. Coque et al. "A Gene Encoding Lysine 6-Aminotransferase, which forms the β-Lactam Precursor α-Aminoadipic Acid, is Located in the Cluster of Cephamycin Biosynthetic Genes in *Nocardia Lactamdurans*", vol. 173, No. 19, pp. 6258-6264, Oct. 1991.

J. F. Martin, "New Aspects of Genes and Enzymes for β-lactam Antibiotic Biosynthesis", Applied Microbiology and Biotechnology, vol. 50, No. 1, pp. 1-15, Jul. 1998.

B. M. Wickwire et al., "Pipecolic Acid Biosynthesis in *Rhizoctonia Leguminicola*", The Journal of Biological Chemistry, vol. 265, No. 25, pp. 14742-14747, Sep. 5, 1990.

L-H. Malmberg et al., "Precursor Flux Control through Targeted Chromosomal Insertion of the Lysine ε-Aminotransferase (lal) Gene in Cephamycin C Biosynthesis", Journal of Bacteriology, vol. 175, No. 21, pp. 6916-6924, Nov. 1993.

K. Irie et al., "Stereoselective Nucleophilic Substitution of 6-Methoxy-1-Methoxycarbonlpipecolate: Enantioselective Synthesis of (+)-Sedamine from L-Lysine", J. Chem. Soc. Chem. Commun., pp. 633-635, 1985.

V. Rodwell, "Pipecolic Acid", Method of Enzymol., 178, pp. 174-188, 1971.

M. Rothstein et al., "The Conversion of Lysine to Pipecolic Acid in the Rat", J. Biol. Chem., vol. 211, pp. 851-858, 1954.

Journal of the American Chemical Society, vol. 74, No. 11, p. 2949, 1952.

A. Aspen et al. "Conversion of α-Aminoadipic Acid to L-Pipecolic Acid by *Aspergillus nidulans*", Biochemistry, vol. 1, pp. 606-612, 1962.

K. Soda et al., "L-Lysine-α-Ketoglutarate Aminotransferase. I. Identification of a Product. Δ'-Piperideine-6-Carboxylic Acid", Biochemistry, vol. 7, pp. 4102-4109, 1968.

H. Misono et al., "Properties of L-Lysine ε-Dehydrogenase from *Agrobacterium tumefaciens*", J. Biochem. vol. 105, pp. 1002-1008, 1989.

C. Payton et al., "$\Delta^1$-Piperideine-2-Carboxylate Reductase of *Pseudomonas putida*", J. Bacteriology, vol. 149, No. 3, pp. 864-871, 1982.

\* cited by examiner

PROCESS FOR THE BIOLOGICAL PRODUCTION OF L-PIPECOLIC ACID

This application is a 371 of PCT/JP00/09137, filed on Dec. 22, 2000 and claims foreign priority under 35 U.S.C, 119(a–d) to Japan 11/37389, filed Dec. 28, 1999.

TECHNICAL FIELD

This invention relates to a biological process for the production of L-pipecolic acid (or 2-piperidinecarboxylic acid or L-homoproline) and to recombinant strains of *Escherichia coli* or coryneform bacteria which can conveniently be used for the process.

BACKGROUND ART

L-Pipecolic acid is important as a raw material for the synthesis of drugs. At present, L-pipecolic acid is being produced by synthesis from L-lysine (J. Chem. Soc. Chem. Commun., 1985, pp. 633–635) or by the optical resolution of DL-pipecolic acid prepared by synthesis from picolinic acid (Method of Enzymol., 17B, pp. 174–188, 1971). As methods for optical resolution, there are known a diastereomer salt method using D-tartaric acid and an enzymatic method in which D-amino acid oxidase derived from pig liver is used to decompose the D-isomer while leaving the L-isomer.

On the other hand, it is known that L-pipecolic acid is produced in animals (J. Biol. Chem., Vol. 211, p. 851, 1954), plants (J. Amer. Chem. Soc., Vol. 74, p. 2949, 1952) and microorganisms (Biochemistry, Vol. 1, pp. 606–612, 1926; Japanese Patent Laid-Open No. 38781/'94). However, since the amount of L-pipecolic acid accumulated therein is small, no process for the production of L-pipecolic acid by using these organisms has been put to practical use. From previous investigations on the metabolism of L-lysine, it is known that delta-1-piperideine-6-carboxylic acid (hereinafter also referred to as P6C) is formed from L-lysine through a transamination reaction by lysine 6-aminotransferase (hereinafter also referred to as LAT) (Biochemistry, Vol. 7, pp. 4102–4109, 1968) or by the action of L-lysine 6-dehydrogenase (J. Biochem., Vol. 105, pp. 1002–1008, 1989).

It has been reported P6C can be chemically converted into L-pipecolic acid by hydrogenation using platinum oxide (Biochemistry, Vol. 7, pp. 4102–4109, 1968), but there is no report about the formation of L-pipecolic acid by the biological or enzymatic reduction of P6C. Moreover, a metabolic pathway is supposed in which *Pseudomonas putida* produces L-pipecolic acid from D-lysine via delta-1-piperideine-2-carboxylic acid. It is also difficult to utilize such biological pathways for the mass production of L-pipecolic acid.

In the above-described process involving the optical resolution of DL-pipecolic acid prepared by chemical synthesis, the optical resolving agent used is expensive and a complicated procedure is required. Moreover, in the process using an enzyme for purposes of optical resolution, the use of a purified enzyme is also expensive. Because of these disadvantages, both processes are not efficient from an industrial point of view and cannot produce L-pipecolic acid cheaply.

Furthermore, conventional processes for the production of L-pipecolic acid by using microorganisms have not been put to practical use because the amount of L-pipecolic acid accumulated is small.

DISCLOSURE OF THE INVENTION

The present inventors have now found that pyrroline-5-carboxylate reductase [EC 1.5.1.2], which reduces delta-1-pyrroline-5-carboxylic acid to L-proline as shown below,

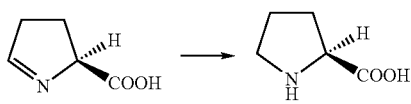

can also reduce P6C to the corresponding L-pipecolic acid efficiently as shown below.

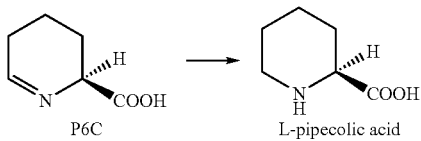

Moreover, it has also been found that this reduction system may be used by combining it conveniently with other biological P6C production systems.

The present invention is based on these findings and provides a means for producing L-pipecolic acid efficiently by utilizing the action of pyrroline-5-carboxylate reductase.

Accordingly, the present invention relates to a process for the production of L-pipecolic acid which comprises the step of reducing delta-1-piperideine-6-carboxylic acid (P6C) by the use of pyrroline-5-carboxylate reductase.

In a preferred embodiment of the present invention, the P6C reduction step is combined with the step of converting L-lysine into P6C by the use of lysine 6-aminotransferase (LAT).

The present invention also relates to a recombinant strain of *Escherichia coli* or a coryneform bacterium which contains a gene encoding LAT in expressible form.

BEST MODE FOR CARRYING OUT THE INVENTION

Figure 1:
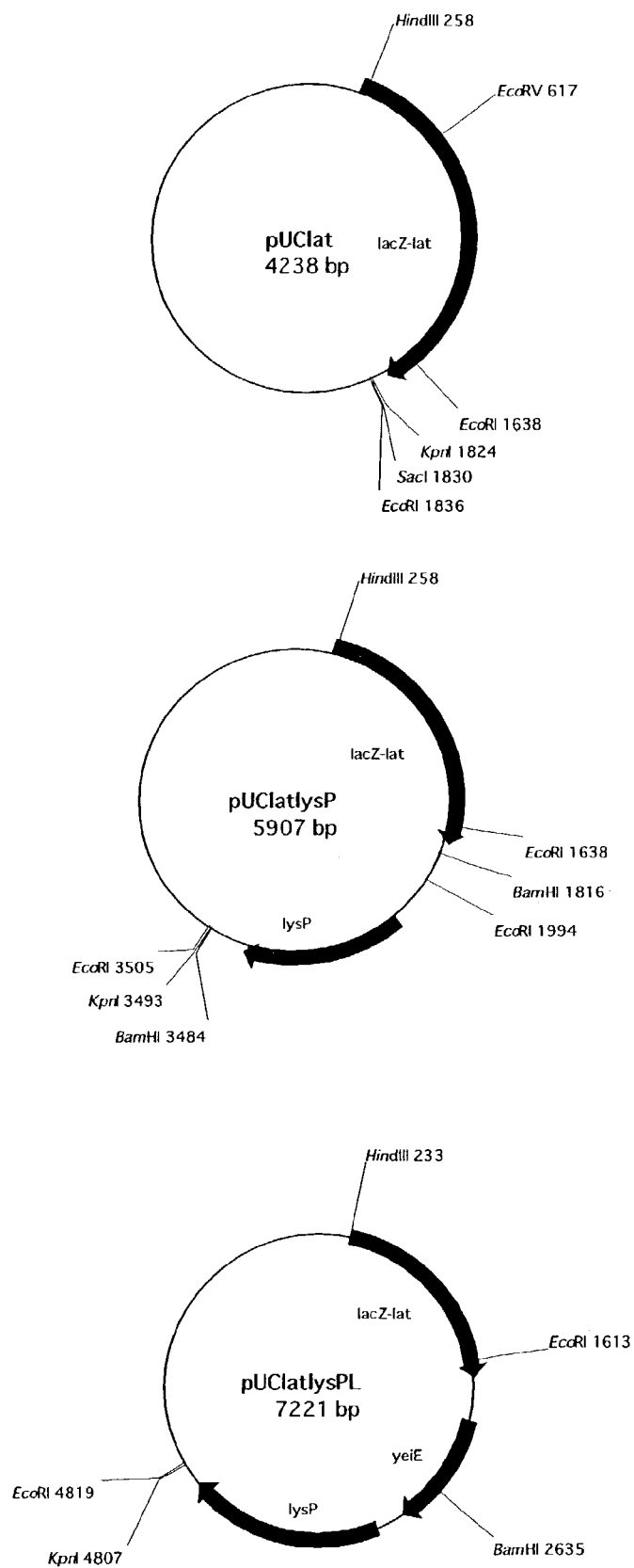
FIG. 1 is a schematic view of a plasmid related to the present invention which has been constructed in order to produce L-pipecolic acid from L-lysine in *Escherichia coli*

The term "exogenous gene" as used herein means a gene derived from a cell different from the mentioned cell itself, whether the cell is similar or dissimilar to the mentioned cell or bacterium.

Pyrroline-5-carboxylate reductase (EC 1.5.1.2; hereinafter also referred to as P5C reductase), which is used in the present invention, is commonly known to be an enzyme which participates in a metabolic pathway for synthesizing proline from arginine or glutamic acid. As described above, this enzyme has an activity for reducing delta-1-pyrroline-5-carboxylic acid to proline with the aid of the reduced form of nicotinamide adenine dinucleotide (NADH) or the reduced form of nicotinamide adenine dinucleotide phosphate (NADPH). It is known that P5C reductase is widely distributed in a great variety of bacteria, plants and animals.

P5C reductase that can be used in the present invention is not limited by its origin, so long as it has an activity for reducing P6C to L-pipecolic acid. P5C reductase may be used in any desired form selected from preparations such as a purified enzyme and a cell lysate, and from living cells. When a preparation is used, the addition of NADH or NADPH may sometimes be needed to carry out the reduction in accordance with the present invention.

Delta-1-piperideine-6-carboxylic acid (P6C), which is to be reduced by the use of P5C reductase according to the present invention, corresponds to a compound obtained when 2-aminoadipic acid 6-semialdehyde formed from L-lysine by the action of lysine 6-aminotransferase (LAT) undergoes nonenzymatic ring closing with the elimination of water. Since this semialdehyde is usually considered to be present in an aqueous solution as an equilibrium mixture with P6C, it is understood that P6C and the semialdehyde are equivalent to each other in the reaction system of the present invention. Accordingly, P6C itself, a mixture of P6C and the semialdehyde, or the semialdehyde itself may be added to the reaction system of the present invention, and all of these embodiments are comprehended in the present invention.

As P6C (or 2-aminoadipic acid 6-semialdehyde), there may be used any of the products prepared by various means including chemical synthesis and biological means. However, from the viewpoint of the economical production of L-pipecolic acid that is a particular optical isomer, it is preferable to use P6C having a steric configuration corresponding to that of L-pipecolic acid (specifically, with respect to the asymmetric carbon atom located at the 2-position).

The step of reducing P6C according to the present invention is carried out by making P5C reductase act on P6C under conditions which allow ordinary enzyme reactions to proceed. As described above, P5C reductase may be made to act on P6C in any desired form selected from preparations such as a purified enzyme and a cell lysate, and from living cells. However, in view of the fact that a coenzyme such as NADH or NADPH participates in the aforesaid reaction, it is preferable to use a cell lysate or living cells themselves. As the cells, it is especially preferable to use cells of *Escherichia coli* or a coryneform bacterium, among microorganisms exhibiting P5C reductase activity capable of converting (or reducing) P6C into L-pipecolic acid. It is known that the proC gene encoding P5C reductase is present in *Escherichia coli*, and the sequence of proC and its expression have been reported (see A. H. Deutch et al., Nucleic Acids Research, Vol. 10, 1982, 7701–7714).

Accordingly, in a preferred embodiment of the present invention, P6C can be reduced to L-pipecolic acid by incubating *Escherichia coli* having P5C reductase activity, or *Escherichia coli* or another microorganism containing the aforesaid proC gene in expressible form, together with P6C under conditions which allow these microorganisms to live and produce P5C reductase activity. As used herein, the expression "containing or integrating a particular gene in expressible form" means that the gene is integrated into a chromosome of a host cell, if necessary, together with a promoter, a regulator and the like; or that the gene is integrated into an expression vector together with a suitable promoter and the like, and then introduced into a host cell. The aforesaid conditions which allow the microorganisms to produce P5C reductase activity refer to conditions under which the respective microorganisms are viable and preferably culture conditions under which they can grow. These conditions are well known to those skilled in the art, and it would be easy for the those skilled in the art to determined the conditions with reference to the examples which will be given later.

The desired reaction may be carried out by adding P6C directly to a suspension or culture of a microorganism as described above. However, according to the present invention, it is preferable to feed P6C to the aforesaid reduction step using P5C reductase by combining it with the step of converting readily available L-lysine into P6C by the use of lysine 6-aminotransferase (LAT). Where *Escherichia coli* is used as a source of P5C reductase in such a combination, it is usually necessary to use a LAT enzyme system derived from foreign cells in combination with the enzyme system of *Escherichia coli*, because an enzyme system catalyzing the process of converting L-lysine into P6C is not present in *Escherichia coli* or, even if it is present, its activity is very low. LAT that can be used in such a combination is not limited by its origin, provided that it has an activity for converting L-lysine into P6C. A preferred example is LAT derived from *Flavobacterium lutescens*. Typical strains (e.g, IFO 3084 strain) of this microorganism are usually used for the bioassay of L-lysine and are known to have LAT activity [Soda et al., Biochemistry, 7(1968), 4102–4109; Ibid., 4110–4119]. Certain strains of *F. lutescens* have the ability to oxidize P6C to α-aminoadipic acid by the action of delta-1-piperideine-6-carboxylate dehydrogenase possessed thereby [Biochem. J. (1977), 327, 59–64]. Moreover, there is a possibility that L-pipecolic acid formed from P6C by P5C reductase or P6C reductase activity may be converted into other compounds through a further metabolic pathway. Consequently, when the enzyme system of this bacterium is used, it may usually happen that the conversion of L-lysine into L-pipecolic acid cannot be achieved or, even if this conversion occurs, L-pipecolic acid is not accumulated. Accordingly, in order to accomplish the purpose of the present invention, it is preferable to use a combination of enzyme systems derived from different types of cells (or microorganisms) as described above. Microorganisms having such a combination of enzyme systems include, but are not limited to, the aforesaid *Escherichia coli* into which, for example, the lat gene of *F. lutescens* encoding LAT is introduced in expressible form; conversely, *F. lutescens* into which the proC gene of *Escherichia coli* is introduced; and host microorganisms which can be suitably used for other purpose of the present invention and in which both lat and proC are introduced in expressible form. Each gene may be introduced into the host by means of a recombinant plasmid, or may be integrated directly into a chromosome of the host in expressible form. When *F. lutescens* is used as the host, there is a possibility that this microorganism may metabolize the formed L-pipecolic acid through a further metabolic pathway. Consequently, it may be necessary to use a variant in which such a metabolic pathway is blocked. As the enzyme system suitable for the purpose of converting L-lysine into L-pipecolic acid according to the present invention, an enzyme system constructed by using *Escherichia coli* (also serving as a source of proC in some cases) as the host and introducing thereinto at least the lat of *F. lutescens* can conveniently be used owing to the stability of the system, its ease of treatment, its high conversion efficiency and the like. Furthermore, when *Escherichia coli* is used as the host, an exogenous proC gene may be introduced in addition to the lat gene. Especially for the purpose of facilitating the incorporation of the starting material (i.e., L-lysine) into bacterial cells, it is preferable to introduce an exogenous gene encoding the lysine-specific incorporation (or permeation) enzyme of *Escherichia coli* (also referred to as a gene participating in the incorporation of lysine). Typical examples of such a gene include, but are not limited to, the gene (lysP) encoding a lysine-specific permease, and the genes (argT, hisP and hisQ) encoding proteins constituting the LAO system participating in the incorporation of lysine, arginine and ornithine. For example, according to J. Bacteriol., Vol. 174, 3242–3249, 1992, it is suggested that *Escherichia coli* into which the lysP gene has been introduced by means of a multicopy plasmid shows a 20-fold increase in lysine incorporation rate.

The above-described systems, which comprise combinations of enzyme systems or genes and can be used in the present invention, may be constructed or prepared according to techniques which are related to cytobiology, cell culture, molecular biology, microbiology and recombinant DNAs and are commonly used per se by those skilled in the art. As to these techniques, reference may be made, for example, to Molecular Cloning—A Laboratory Manual, 2nd Ed., ed. by Sambrook, Fritsch and Maniatis (Cold Spring Harbor Laboratory Press, 1989); DNA Cloning, Volumes I and II (D. N. Glover ed., 1985); Oligonucleotide Synthesis (M. J. Gait ed., 1984); Mullis et al., U.S. Pat. No. 4,683,195; and Nucleic Acid Hybridization (B. D. Hames & S. J. Higgins eds., 1984).

The construction or preparation of enzyme systems or microorganisms which can preferably be used in the present invention is more specifically described below in connection with embodiments in which *Escherichia coli* (hereinafter abbreviated as *E. coli*). However, it is to be understood that the present invention is not limited by these embodiments.

Host-Vector System:

Commercially available strains and vectors may be suitably used. The embodiments described herein are such that *Escherichia coli* BL21(DE3), *Escherichia coli* BL21 or *Escherichia coli* C600 strain is used as the host and a pET or pUC system is used as the vector. As other vectors, the vectors conforming to "Guidelines for the Industrialization of Recombinant DNA Technology" (the Ministry of International Trade and Industry), Guideline, Section 2, No. 3, 2.(2) may preferably be used.

Cloning and Expression of the lat Gene:

LAT was purified from the culture supernatant of *F. lutescens* IFO 3084 strain by hydrophobicity chromatography, ion exchange chromatography and gel permeation chromatography. The enzyme activity of LAT was measured by a colorimetric method using o-aminobenzaldehyde (Biochemistry, Vol. 7, pp. 4102–4109, 1968). The N-terminus of the purified LAT was determined to be KLLAPLAPLRA-HAGTRLTQGL. On the basis of this amino acid sequence, mix primers were designed and used in PCR to amplify DNA fragments of lat from the genomic DNA of *F. lutescens* IFO 3084 strain. Then, on the basis of the DNA fragments thus obtained, the entire lat gene of about 1.6 kbp size was obtained by inverse PCR. The DNA sequence of lat and the amino acid sequence of LAT are shown in SEQ ID NO:1. For further details about the cloning of the lat gene, reference may be made to International Application PCT/J99/04197 that is copending with the present application, if necessary.

From the so-determined base sequence of the lat gene, the following forward DNA primer in which a region in the neighborhood of the N-terminal ATG of the lat gene was altered to a NdeI site ETlaNdeF: TCCATATGTCCCTTCTTGCCCCGCTCGCCC
(SEQ ID NO:2)

and the following reverse DNA primer in which a region downstream of the termination codon thereof was altered to a BamHI site ETlaBamR: GCGGATCCTGTTGCCGCTGGTGCCGG- (SEQ ID NO:3)
GCAG were prepared. Using these primers, PCR was carried out to amplify the lat gene region of about 1.6 kbp size. This amplified fragment was digested with the restriction enzymes NdeI and BamHI to prepare an insert DNA solution. On the other hand, the expression vector pET11a (manufactured by Novagen) was digested with the restriction enzymes NdeI and BamHI, and subjected to a ligation reaction with the insert DNA solution by means of Ligation Kit version 2 (manufactured by TaKaRa). The plasmid thus obtained was named pETlat. pETlat is a plasmid designed so as to bring about the expression of natural LAT protein. *E. coli* BL21(DE3) was transformed with this plasmid, and the resulting strain was named *E. coli* BL21(DE3)pETlat strain.

Next, the expression vector pET11a was replaced by pUC19, and *E. coli* BL21 strain was used as the host. From the aforesaid base sequence of the lat gene, the following forward DNA primer in which a region in the neighborhood of the N-terminal ATG of the lat gene was altered to a HindIII site lathiF19: ATAAGCTTGTCCCTTCTTGCCCCGCTCGC
(SEQ ID NO:4)

was prepared and the following reverse DNA primer in which a region downstream of the termination codon thereof was altered to a BamHI site ETlaBamR: GCGGATCCTGTTGCCGCTGGTGCCGGGCAG
(SEQ ID NO:3)

were prepared. Using these primers, PCR was carried out to amplify the lat gene region of about 1.6 kbp size. This amplified fragment was digested with the restriction enzymes HindIII and BamHI to prepare an insert DNA solution. On the other hand, the vector pUC19 was digested with the restriction enzymes HindIII and BamHI, and subjected to a ligation reaction with the insert DNA solution by means of Ligation Kit version 2 (manufactured by TaKaRa). The plasmid thus obtained was named pUClat (see FIG. 1). pUClat is a plasmid designed so as to bring about the expression of LacZ-LAT fusion protein. *E. coli* BL21 was transformed with this plasmid, and the resulting strain was named *E. coli* BL21pUClat strain.

When each of *E. coli* BL21(DE3)pETlat strain and *E. coli* BL21pUClat strain was cultured in a culture medium (1.5% Bacto tryptone, 3.0% yeast extract, 0.5% glycerol, pH 7) containing L-lysine, the accumulation of L-pipecolic acid in the culture medium was observed in both cases. This means that an enzyme capable of reducing P6C formed from L-lysine by a transamination reaction catalyzed by LAT is present in *Escherichia coli* used as the host.

A search was made for this P6C reduction enzyme. From the genetic information on the whole genome of *Escherichia coli*, it was supposed that the P5C reduction enzyme also reduced P6C. Then, the role of proC in L-pipecolic acid production was investigated by using *E. coli* RK4904 strain (obtained from the *E. coil* Genetic Stock Center of Yale University) that is a proC-deficient proC32 mutant strain. First, in order to examine the effect of proC (see SEQ ID NO:5), it was tried to introduce proC into pUClat. The following DNA primers having a KpnI site attached to an end thereof were prepared.

```
procKpnF: AGGGTACCATAAAATCGCGCATCGTCAGGC
(SEQ ID NO:6)

procKpnR: CCGGTACCGCCACAGGTAACTTTACGGATT
(SEQ ID NO:7)
```

Using these primers, PCR was carried out to amplify a proC-containing fragment of about 1.5 Kbp size. This amplified fragment of about 1.5 Kbp size was digested with the restriction enzyme KpnI to prepare an insert DNA solution. On the other hand, the plasmid pUClat was digested with the restriction enzyme KpnI, and subjected to a ligation reaction with the insert DNA solution by means of Ligation Kit version 2 (manufactured by TaKaRa). The resulting plasmid in which lat and proC are ligated so as to be oriented in the forward direction was named pUClatproC.

*E. coli* RK4904 was transformed with this plasmid, and the resulting strain was named *E. coli* RK4904pUClatproC strain. Moreover, a plasmid having proC alone was prepared. Specifically, pUClatproC was digested with the restriction enzymes BamHI and HindIII, blunt-ended by means of Blunting Kit (manufactured by TaKaRa), and subjected to a self-ligation reaction. The plasmid thus obtained was named pUCproC. *E. coli* RK4904 was transformed with this plasmid, and the resulting strain was named *E. coli* RK4904pUCproC strain. When L-pipecolic acid production tests were carried out by using the so-constructed *E. coli* RK4904pUC19 strain, *E. coli* RK4904pUClat strain, *E. coli* RK4904pUCproC strain and *E. coli* RK4904pUClatproC strain, *E. coli* RK4904pUClatproC strain alone showed the accumulation of L-pipecolic acid and the other strains showed no production of L-pipecolic acid.

These results indicate that L-pipecolic acid is produced only when both lat and proC are expressed in *E. coli* and that P5C reductase, which is a protein encoded by proC, also reduces P6C. To the present inventors' knowledge, no enzyme capable of reducing P6C has been described in the literature, and the present description discloses such an enzyme for the first time.

Cloning of the lysP Gene and Cointegration of the lysP and lat Genes:

According to the aforementioned J. Bacteriol., Vol. 174, 3242–3249, 1992, there is a possibility that the rate of the incorporation of lysine into *Escherichia coli* determines the rate of the production of L-pipecolic acid by *Escherichia coli*. Now, as described below, it was tried to introduce the lysP gene encoding a lysine-specific permease into the plasmid pETlat. From the genetic information on the sequence of the lysP gene of *Escherichia coli* (see SEQ ID NO:8), the following DNA primers having Bg/II and BamHI sites attached to an end thereof were prepared.

```
lysPBgBmF: TGAGATCTGGATCCTGCGTGAACGCGGTTC
(SEQ ID NO:9)

lysPBgBmR: GCAGATCTGGATCCCAGAAAGCCGGAACAG
(SEQ ID NO:10)
```

For the cloning of lysP, PCR was carried out by using these primers to amplify a lysP containing fragment of about 2.2 Kbp size. This amplified fragment of about 2.2 Kbp size was digested with the restriction enzyme Bg/II to prepare an insert DNA solution. On the other hand, pETlat was digested with the restriction enzyme Bg/II, and subjected to a ligation reaction with the insert DNA solution by means of Ligation Kit version 2 (manufactured by TaKaRa). The so-constructed plasmid in which lat and lysP are ligated so as to be oriented in the opposite directions was named pETlatlysP. *E. coli* BL21(DE3) was transformed with this plasmid, and the resulting strain was named *E. coli* BL21(DE3)pETlatlysP strain. When L-pipecolic acid production tests were carried out by using this *E. coli* BL21(DE3)pETlatlysP strain and *E. coli* BL21(DE3)pETlat strain (obtained by transformation with the previously prepared pETlat), it was confirmed that *E. coli* BL21(DE3)pETlatlysP strain produced L-pipecolic acid in a three times greater amount than *E. coli* BL21(DE3) pETlat strain.

Moreover, the aforesaid amplified fragment of about 2.2 Kbp size was digested with the restriction enzyme BamHI to prepare an insert DNA solution. On the other hand, pUClat was digested with the restriction enzyme BamHI, and subjected to a ligation reaction with the insert DNA solution by means of Ligation Kit version 2 (manufactured by TaKaRa). The so-constructed plasmid in which lat and lysP are ligated so as to be oriented in the forward direction was named pUClatlysP (see FIG. 1). *E. coli* BL21 was transformed with this plasmid, and the resulting strain was named *E. coli* BL21pUClatlysP strain. When L-pipecolic acid production tests were carried out by using this *E. coli* BL21pUClatlysP strain and *E. coli* BL21pUClat strain, it was confirmed that *E. coli* BL21pUClatlysP strain produced L-pipecolic acid in a three times greater amount than *E. coli* BL21pUClat strain. Thus, when *Escherichia coli* is used as the host, it is desirable to introduce the lysP gene thereinto. *E. coli* BL21pUClatlysP strain in accordance with the present invention was deposited on Dec. 20, 1999 with the National Institute of Bioscience and Human-Technology, the Agency of Industrial Science and Technology (1–3, Higashi 1-chome, Tsukuba City, Ibaraki Prefecture, Japan) and assigned the accession number FERM P-17681. Thereafter, the aforesaid deposition was transferred to the international deposition department of the institute under the provisions of the so-called Budapest Treaty and assigned the accession number FERM BP-7326.

Introduction of the yeiE Gene:

In order to improve the L-pipecolic acid-producing ability of BL21pUClatlysP strain, it was tried to further enhance the activity of lysP. The *E. coli* genome project has revealed the DNA sequence of a region around lysP This indicates that the yeiE gene (see SEQ ID NO:11) arranged in tandem with lysP is present on the upstream side of lysP. From its amino acid sequence, it is suggested that yeiE is a lysR type transcriptional regulator sequence which is frequently retained in bacteria. Since it was supposed that this yeiE might control the transcription of lysP, it was expected that the L-pipecolic acid-producing ability could be improved by integrating both yeiE and lysP into a plasmid to increase the transcription of lysP and thereby enhance the ability to incorporate L-lysine.

The plasmid pUClatlysPL was constructed as described below. The following forward DNA primer having a Bg/II site attached to an end thereof

ATAGATCTCTTGTTGCCTAAAACCATCCCCAA (SEQ ID NO:12)

and the following reverse DNA primer having a KpnI site attached to an end thereof

GTGGTACCCCCCAGAAAGCCGGAACAGCCTC (SEQ ID NO:13)

were prepared. Using these primers, PCR was carried out to amplify a yeiE- and lysP-containing region of about 3 Kbp size. This amplified fragment was digested with the restriction enzymes Bg/III and KpnI to prepare an insert DNA solution. On the other hand, pUClatlysP was digested with the restriction enzymes BamHI and KpnI, and subjected to a ligation reaction with the insert DNA solution by means of Ligation Kit version 2 (manufactured by TaKaRa). The plasmid thus obtained was named pUClatlysPL (see FIG. 1). E. coli BL21 was transformed with this plasmid, and the resulting strain was named E. coli BL21pUClatlysPL strain.

Cloning and Introduction of the argT Gene:

It is known that the expression of lysP is suppressed at high lysine concentrations and induced at low lysine concentrations [J. Bacteriol. (1996), Vol., 178, 5522–5528]. Accordingly, it was planned to introduce an additional gene participating the incorporation of lysine into cells. Up to this time, it is known that a system for the incorporation of lysine, arginine and ornithine into cells (i.e., the LAO system) is present in Escherichia coli [Journal of Biological Chemistry, Vol. 265, pp. 1783–1786 (1990)]. Moreover, since the argT gene of Escherichia coli clarified by the genome project has high homology with the argT gene of Salmonella typhimurium shown to participate in the LAO system [Proc. Natl. Acad. Sci. USA, Vol. 78, pp. 6038–6042 (1981)], it was expected that the argT gene of Escherichia coli was highly likely to participate in the incorporation of lysine.

Now, in order to examine the effect of argT, the plasmid pUClatargT having lat and argT integrated thereinto were constructed as described below. The following primers were prepared.

argTkpnF: TCGGTACCTCGACATTTTGTTTCTGCC
(SEQ ID NO:14)

argTkpnR: ATGGTACCATAAAATTGACCATCAAGG
(SEQ ID NO:15)

Using these primers and a template comprising the genomic DNA of Escherichia coli, PCR was carried out to amplify argT. The reaction conditions were such that one cycle consisted of 98° C./20 seconds, 60° C./30 seconds and 68° C./1 minute, and this cycle was repeated 25 times. This amplified fragment of about 1.5 Kbp was digested with the restriction enzyme KpnI and inserted into the KpnI site of pUClatlysPL. Moreover, the tetracycline resistance gene was inserted into the ScaI site of the resulting plasmid. Specifically, the following primers having a ScaI site added to an end thereof were prepared.

TetF: TTAGTACTCTTATCATCGATAAGCTTTAAT (SEQ ID NO:16)

TetR: GCAGTACTACAGTTCTCCGCAAGAATTGAT (SEQ ID NO:17)

Using these primers and a template comprising pBR322, PCR was carried out to amplify the tetracycline resistance gene. This gene was inserted into the ScaI site present in the ampicillin resistance gene of pUClatlysPL, and the resulting plasmid was named pUClatlysPLargT-tet. This plasmid was introduced into E. coli BL21 strain, and the resulting strain was named E. coli BL21pUClatlysPLargT-tet strain. The DNA sequence and amino acid sequence of argT are shown in SEQ ID NO:18.

Construction and Expression of a lat Transformant in a Coryneform Bacterium:

As described above, there has been established an L-pipecolic acid production system based on the conversion of L-lysine into L-pipecolic acid by the use of a lat-expressing strain of Escherichia coli. In this system using a recombinant strain of Escherichia coli, it has been suggested that, in some cases, the incorporation of L-lysine into cells determines the rate of production of L-pipecolic acid. Accordingly, it may be desirable to provide a direct L-pipecolic acid-producing bacterium which produces L-lysine by itself and converts it into pipecolic acid without requiring the addition of L-lysine to the culture medium. This provision can be accomplished according to the following strategy. L-lysine is produced in large amounts by fermentation with Corynebacterium glutamicum. Then, if lat can be integrated into the pC2 plasmid [PLASMID, Vol. 36, 62–66 (1996)] established as a vector system for C. glutamicum and this plasmid can be introduced into C. glutamicum ATCC31831 strain to bring about the expression of lat, L-lysine biosynthesized in its cells will be converted into P6C and this P6C will further be converted into pipecolic acid by the action of pyrroline-5-carboxylate reductase produced by the expression of proC encoded in the genome of C. glutamicum. The validity of this strategy can be ascertained, for example, by carrying out the following experiment.

Using the aforesaid plasmid pC2 plasmid, the plasmid pClat for the expression of lat was constructed as described below. The following forward DNA primers were prepared.

ClatBamF: GGGGTACCCATGTCCCTTCTTGCCCCGCT
(SEQ ID NO:19)

ClatBamR: GGGGATCCCGCGGCCTGTTGCCGCTGGT
(SEQ ID NO:20)

Figure 2:
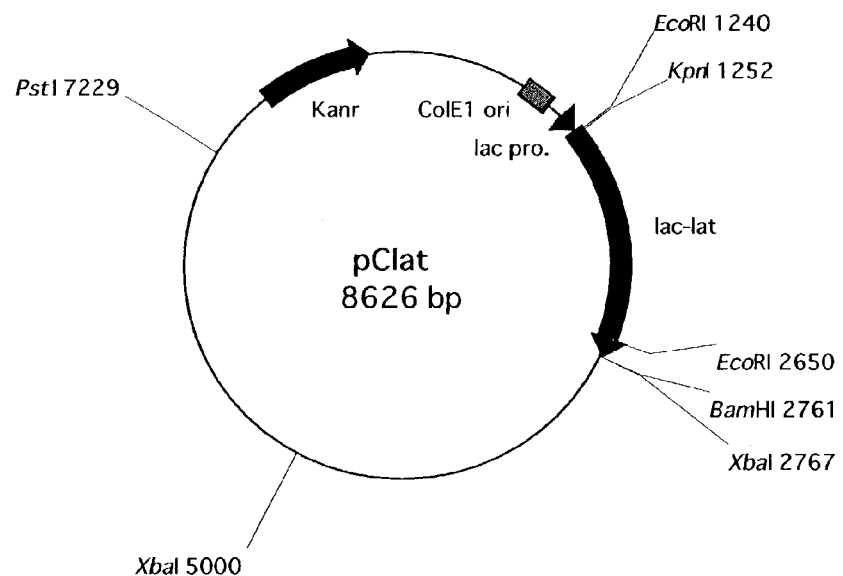
FIG. 2 is a schematic view of a plasmid related to the present invention which has been constructed in order to produce L-pipecolic acid in a coryneform bacterium.

Using these primers and a template comprising the genomic DNA of Flavobacterium lutescens, PCR was carried out to amplify lat. The reaction conditions were such that one cycle consisted of 98° C./20 seconds and 68° C./2 minutes, and this cycle was repeated 25 times. This amplified fragment of about 1.5 Kbp was digested with the restriction enzymes KpnI and BamHI, and ligated into the KpnI and BamHI sites of pC2 (FIG. 2). This plasmid pClat was introduced into E. coli JM109 strain. Using the strain thus obtained, it was confirmed that the conversion of L-lysine into pipecolic acid proceeded, i.e. the strain had LAT activity.

Subsequently, C. glutamicum was transformed with pClat. For example, C. glutamicum was inoculated into 3 ml of L medium and incubated at 32° C. for 17 hours with shaking. 30 μl of the resulting culture was inoculated into 3 ml of L medium and incubated at 32° C. for 2.5 hours with shaking. Then, 1.5 μl of a penicillin G potassium solution (2 mg/ml) was added thereto, and the incubation was continued for an additional 1.5 hours with shaking. The total amount of cells were collected, washed with 5 ml of a 10% glycerol solution, and suspended in 700 μl of a 10% glycerol solution to prepare an electro-cell suspension. 0.2 μl of the plasmid dissolved in a TE solution (200 μg/ml) was added to 200 μl of the electro-cell suspension, and subjected to electroporation under conditions including 12.5 kV/cm, 25 μF and 200 Ω. After 1 ml of L medium was added thereto and this mixture was incubated at 32° C. for 2 hours, the resulting culture was spread over an L plate containing 10 μl/ml of kanamycin, and incubated at 32° C. for 3 days. Desired transformants can be obtained by screening the colonies so formed.

As used herein, the term "coryneform bacterium" comprehends any species that typically belongs to the genus *Corynebacterium*, produces L-lysine, and meets the purposes of the present invention.

Alterations of the Above-Described Genes or DNA Sequences:

According to the present invention, the genes or DNAs encoding the above-described various enzymes, i.e. the gene encoding lysine 6-aminotransferase, the gene encoding pyrroline-5-carboxylate reductase, the gene encoding a lysine-specific incorporation enzyme, and the gene regulating the transcription of lysP, also comprehend any alterations thereof, provided that such alterations can hybridize with the respective genes (see, for example, SEQ ID NO:1, SEQ ID NO:5, SEQ ID NO:8, SEQ ID NO:11 and SEQ ID NO:18) under stringent conditions and the polypeptides produced by the expression thereof have respective desired enzyme activities.

Stringent conditions are well known to those skilled in the art and are described, for example, in the aforementioned manual by Sambrook et al., pp. 9.31–9.62. Such alterations may be made according to per se known techniques such as point mutagenesis, site-directed mutagenesis and chemical synthesis, by examining, as an index, whether they have the deletion or addition of one or more amino acids which are not essential to the desired enzyme activity or exert no adverse influence thereon, or whether they have a substitution between amino acid residues having a similar side chain, such as amino acid residues having a basic side chain (lysine, arginine, histidine, etc.), an acidic side chain (aspartic acid, glutamic acid, etc.), an uncharged polar side chain (glycine, asparagine, glutamine, serine, threonine, tyrosine, cysteine, etc.), a nonpolar side chain (alanine, valine, leucine, isoleucine, proline, phenylalanine, methionine, tryptophan, etc.), a β-branched side chain (e.g., threonine, valine, isoleucine, etc.) or an aromatic side chain (e.g., tyrosine, phenylalanine, tryptophan, histidine, etc.). Moreover, the transformation of host cells with such genes may be carried out according to the previously described procedures or methods which are well known to those skilled in the art.

In order to confirm that the resulting pipecolic acid was the L-form, HPLC using a chiral column (Agric. Biol. Chem., Vol. 52, pp. 1113–1116, 1988) was employed. Using a DAICEL CHIRAL PAK WH (4.6×250 mm; manufactured by Daicel) as the column and a 0.25 mM aqueous solution of copper sulfate as the mobile phase, HPLC was carried out at a column temperature of 50° C. and a flow rate of 1.0 ml/min. Detection was carried out at an ultraviolet wavelength of 243 nm. Under these conditions for HPLC, the retention time of D-pipecolic acid is 11.5 minutes and the retention time of L-pipecolic acid is 15 minutes. When the pipecolic acid produced by the recombinant strains of *Escherichia coli* in accordance with the present invention was analyzed, the retention time of the pipecolic acid so produced was 15 minutes.

EXAMPLES

The present invention is more specifically explained with reference to the following examples.

In these examples, L-pipecolic acid was determined by dansylating it and then subjecting it to high-performance liquid chromatography (hereinafter abbreviated as HPLC) while using proline as an internal standard. Specifically, after the culture supernatant was diluted 100-fold with distilled water, 10 μl was transferred to an Eppen tube, and 200 μl of a 40 mM lithium carbonate buffer (pH 9.5) containing 5 μg/ml proline and 100 μl of an acetonitrile solution containing 3.0 mg/ml dansyl chloride were added thereto. The resulting mixture was stirred and reacted in the dark at room temperature for 2 hours. After 10 μl of 2% methylamine hydrochloride was added thereto with stirring, the resulting supernatant was used as an analytical sample. As to the analytical conditions for HPLC, the column was YMC-Pack ODS-A A-303 (4.6×250 mm; manufactured by YMC), the mobile phase was a 33.2% acetonitrile solution containing 0.003 M L-proline, 0.0015 M copper sulfate and 0.0039 M ammonium acetate (adjusted to pH 7 with aqueous ammonia), elution was carried out at a flow rate of 0.8 ml/min and at room temperature, and detection was carried out at an excitation wavelength of 366 nm and a fluorescence wavelength of 510 nm. Under these conditions, the retention time of L-pipecolic acid was 13 minutes.

Example 1

L-Pipecolic acid production tests were carried out with respect to *E. coli* BL21pUClatlysP (FERM BP-7326) strain, *E. coli* BL21(DE3)pETlatlysP strain, *E. coli* C600pUClatlysP strain and *E. coli* BL21pUClatlysPL strain. Each strain was inoculated into 3 ml of L medium (1.0% polypeptone, 0.5% yeast extract, 0.5% NaCl, 0.1% glucose, pH 7.2) containing 50 μg/ml ampicillin sodium, and incubated at 32° C. overnight with shaking. The resulting cultures were used seed cultures, and 275 μl of each seed culture was inoculated into 27.5 ml of TB medium (0.44% glycerol, 1.33% Bacto-trypton, 2.67% Bacto-yeast extract, 0.21% $KH_2PO_4$, 1.14% $K_2HPO_4$) containing 100 μg/ml ampicillin sodium, and incubated at 32° C. for 4.5 hours with shaking. In the culture of a microorganism formed with a pET vector, such as *E. coli* BL21(DE3)pETlatlysP, 275 μl of 100 mM isopropyl-β-D-thiogalactopyranoside (IPTG) was added for the purpose of inducing lat, and the incubation was continued at 32° C. for an additional 4 hours with shaking. In contrast, when a pUC vector was used, the addition of IPTG was unnecessary. Subsequently, 500 μl of 50% L-lysine hydrochloride and 250 μl of 50% glycerol dissolved in a phosphate buffer (pH 6.8) were added to each culture, and the incubation was continued at 32° C. with shaking. Furthermore, 15 hours, 39 hours, 63 hours, 87 hours, 120 hours and 159 hours after the addition of L-lysine hydrochloride, 500 μl of 50% L-lysine hydrochloride and 500 μl of 50% glycerol dissolved in a phosphate buffer (pH 6.8) were added. One hundred-μl samples were taken after 15 hours, 39 hours, 63 hours, 87 hours, 120 hours, 159 hours and 207 hours, and their pipecolic acid content was determined by HPLC. As a result, each strain accumulated L-pipecolic acid in the culture medium at the following concentration.

| E. coli BL21pUClatlysP | 10 g/l, |
|---|---|
| E. coli BL21(DE3)pETlatlysP | 26 g/l, |
| E. coli C600pUClatlysP | 0.8 g/l, and |
| E. coli BL21pUClatlysPL | 15 g/l. |

Example 2

In order to elucidate the role of P5C reductase in L-pipecolic acid production, the ability to produce L-pipecolic acid was examined with respect to four recombinant strains formed by using proC-deficient *E. coil* RK4904 strain as the host, namely *E. coli* RK4904pUC19 strain, *E. coli* RK4904pUClat strain, *E. coli* RK4904pUCproC strain and *E. coli* RK4904pUClatproC strain. Each strain was inoculated into 3 ml of L medium (1.0% polypeptone, 0.5% yeast extract, 0.5% NaCl, 0.1% glucose, pH 7.2) containing 50 µg/ml ampicillin sodium, and incubated at 32° C. overnight with shaking. The resulting cultures were used seed cultures, and 275 µl of each seed culture was inoculated into 27.5 ml of TB medium (0.44% glycerol, 1.33% Bacto-trypton, 2.67% Bacto-yeast extract, 0.21% $KH_2PO_4$, 1.14% $K_2HPO_4$) containing 50 µg/ml ampicillin sodium, and incubated at 32° C. for 8 hours with shaking. Then, 500 µl of 50% L-lysine hydrochloride and 500 µl of 50% glycerol dissolved in a phosphate buffer (pH 6.8) were added thereto, and the incubation was continued at 32° C. with shaking. A 100-µl sample was taken after 40 hours, and L-pipecolic acid was determined by HPLC. As a result, *E. coli* RK4904pUClatproC strain alone showed the accumulation of 0.765 g/l of L-pipecolic acid, and the other strains showed no accumulation of pipecolic acid.

Example 3

An investigation on the carbon source of the culture medium was carried out by using *E. coli* C600pUClatlysP strain. As to the composition of the culture medium, there were used culture media obtained by substituting various carbon sources for the glycerol of TB medium (0.44% glycerol, 1.33% Bacto-trypton, 2.67% Bacto-yeast extract, 0.21% $KH_2PO_4$, 1.14% $K_2HPO_4$). As carbon sources, glycerol, sodium pyruvate, citric acid, propionic acid, maleic acid, lactic acid and DL-malic acid were examined. 25 ml of each culture medium was placed in a 250-ml Erlenmeyer flask and incubated at 32° C. with shaking. The amount of L-pipecolic acid accumulated after 24 hours of incubation was 4.8 g/l, 3.3 g/l, 2.8 g/l, 2.6 g/l, 3.5 g/l, 4.7 g/l and 4.7 g/l, respectively. This indicates that organic acids can be used as carbon sources in the present invention.

Example 4

Production of L-Pipecolic Acid With Disintegrated Bacterial Cells

Each of *E. coli* RK4904pUC19 strain, *E. coli* RK4904pUClat strain, *E. coli* RK4904pUCproC strain and *E. coli* RK4904pUClatproC strain was inoculated into 3 ml of L medium containing 50 µg/ml ampicillin sodium, and incubated at 32° C. overnight with shaking. The resulting cultures were used seed cultures, and 275 µl of each seed culture was inoculated into 50 ml of L medium containing 50 µg/ml ampicillin sodium, and incubated at 32° C. for 8 hours with shaking. After this culture was centrifuged, the cells were washed with 0.85% NaCl and 2 ml of BugBuster (Novagen) was added thereto. The resulting supernatant was used as a disintegrated cell suspension. To 100 µl of each disintegrated cell suspension was added 1 ml of a 0.2 M phosphate buffer (pH 7.2) containing 20 µmol L-lysine-HCl, 20 µmol 2-ketoglutaric acid, 0.075 µmol pyridoxal phosphate and 200 µmol NADH, followed by standing at 32° C. for 15 hours. 5 µl each of the resulting reaction mixtures were spotted onto a TLC plate (Merck Art. 13143), developed with a developing solvent (1-butanol-acetic acid-water =3:1:1), and then treated with ninhydrin to produce a color. As a result, a spot of L-pipecolic acid was observed for the disintegrated cell suspension of *E. coli* RK4904pUClatproC strain. This indicates that, also in an in vitro reaction, L-pipecolic acid is produced by the action of LAT formed from the lat gene encoded on the plasmid and pyrroline-5-carboxylate reductase formed from proC.

Example 5

Similarly to pUClatlysPLargT-tet, the plasmid pUClatlysPL-tet was constructed by introducing the tetracycline resistance gene into the ScaI site of pUClatlysPL. Using these plasmids, the following conversion reaction was carried out.

Each of the frozen seed cultures of two bacterial strains, *E. coli* BL21 pUClatlysPLargT-tet strain and *E. coli* BL21 pUClatlysPL-tet strain, was inoculated into L medium (3 ml/centrifuge tube) containing 25 µg/ml tetracycline, and incubated at 32° C. for 18 hours on a rotary shaker. Then, 500 µl of each seed cultures was inoculated into TB medium (27.5 ml/centrifuge tube) containing 25 µg/ml tetracycline, and incubated at 32° C. for 24 hours on a rotary shaker. After completion of the incubation, the O.D. at 660 nm was 3.98 and 9.38, respectively. Cells were collected from each of the resulting cultures (4.71 ml and 2.00 ml, respectively). After 1 ml of a 25 mM phosphate buffer (pH 6.8) was added to the collected cells, 20 µl of a 20% L-lysine solution and 20 µl of 20% glycerol were added to initiate the conversion reaction at 32° C. Two hours, 7 hours and 24 hours after the start of the reaction, 100-µl samples were taken and their pipecolic acid and lysine contents were determined by HPLC.

The amounts of pipecolic acid accumulated after 2 hours, 7 hours and 24 hours of the conversion reaction were 0.36 g/l, 0.73 g/l and 2.0 g/l, respectively, for *E. coli* BL21 pUClatlysPLargT-tet strain; and 0.88 g/l, 1.3 g/l and 1.4 g/l, respectively, for *E. coli* BL21 pUClatlysPL-tet strain. Thus, the pipecolic acid production rate of *E. coli* BL21 pUClatlysPL-tet strain decreased gradually, whereas *E. coli* BL21 pUClatlysPLargT-tet strain maintained an almost constant pipecolic acid production rate, though its initial pipecolic acid production rate was somewhat inferior. This pipecolic acid production rate corresponded exactly with the lysine consumption rate. The role of the argT gene in pipecolic acid production was confirmed by these experimental results.

Example 6

A culture test was carried out with respect to the lat transformed strain of a coryneform bacterium, namely *C.* glutamicum ATCC31831 pClat strain. As a control, C. glutamicum ATCC31831 pC2 strain having a lat-free plasmid was also tested in the same manner. After these two strains were grown in agar plates to form colonies, these colonies were inoculated into test tubes in which 3 ml of L medium containing 20 µg/ml kanamycin was placed, and incubated at 32° C. for 18 hours on a rotary shaker. 275 µl each of the resulting cultures were inoculated into 250-ml Erlenmeyer flasks in which 27.5 ml of TB medium containing 20 µg/ml kanamycin was placed, and incubated at 32° C. on a rotary shaker. Five hours, 15 hours, 39 hours and 63 hours after the start of the incubation, 550 µl portions of 50% glycerol dissolved in a phosphate buffer (pH 6.8) were added thereto. The incubation was discontinued 135 hours after the start of the addition of glycerol, and the pipecolic acid content of the culture supernatant was determined by HPLC. As a result, C. glutamicum ATCC31831 pClat strain accumulated about 0.7 g/l of pipecolic acid in 135 hours after the first addition of glycerol. On the other hand, the control (C. glutamicum ATCC31831 pC2 strain) showed no accumulation of pipecolic acid. This indicates that the lat gene introduced by means of a plasmid is also expressed in the coryneform bacterium and that the pyrroline-5-carboxylate reductase (proC gene) of the coryneform bacterium reduces P6C converted from lysine by the action of LAT and thereby produces pipecolic acid.

SEQUENCE LISTING

<160> NUMBER OF SEQ ID NOS: 20

<210> SEQ ID NO 1
<211> LENGTH: 2663
<212> TYPE: DNA
<213> ORGANISM: Flavobacterium lutescens
<220> FEATURE:

<400> SEQUENCE: 1

```
cccgggtgtc attgaatacc agcaggtcgc caggttgcag cagctggtcc agatcgcgca      60
cctggcgatc ctccagcgca gccggtgccg gcggcaccag cagcaggcgg ctggccgaac     120
gctccggcag cggcgcctgg gcaatcagtt cgggaggcag gtggtaggca aaatcggact     180
tcttcaacgc cggcagctcg atacaacggg ggcgtcagtt tacgcccctg taccgcctgt     240
gccctcaccg ctcgaacttg gtgcccagga tcaccgccgt ggtggtgcgc tcgaccccat     300
cagtggcgcc gatggcatcg gtcagctcgt ccatcgccgc cacgccatcg acggcggca      360 tcgccaccag gtcatgcgcg ccactgaccg aatgcaggct gcgcaccgca gcaatggcct     420
gcagcgcccg cacgaccgcc ggcattttct tcggcatcac ggtgatggag atatgcgcgc     480
ggacctgctg gcgctccatc gcctggccaa ggcgcacggt gtagccggcg attattccgc     540
tgtgctgcag ccgctcgatc cggctctgca ccgtggtccg cgacaccccg agccggcgcg     600
ccagcgccgc ggtcgaggcg cgcgcatcct cacgcaacag gtcaagcaac tgtgcatccg     660
cctgggaaat ggtcactttg tcgaaaacct ttcgtcaatc cgccgaaacc ggccattgat     720
ttgagcagat tcgcactgcc atttgtagtg cgttaacggt tacaactaac actagacaca     780
atcagcacgg attcagc atg tcc ctt ctt gcc ccg ctc gcc ccg ctc cgc        830
                    Met Ser Leu Leu Ala Pro Leu Ala Pro Leu Arg
                      1               5                  10 gcc cat gcc ggc acc cgc ctt acc cag ggc ctg tct gac ccg cag gtc       878
Ala His Ala Gly Thr Arg Leu Thr Gln Gly Leu Ser Asp Pro Gln Val
           15                  20                  25 gag cag ctg gcc gcc aac cac cct gac ctg cgc gcc gcc atc gac gcc       926
Glu Gln Leu Ala Ala Asn His Pro Asp Leu Arg Ala Ala Ile Asp Ala
       30                  35                  40 gct gcc gac gaa tac gcg cgc atc aaa ccg cag gcc gcg gca ttg ctg       974
Ala Ala Asp Glu Tyr Ala Arg Ile Lys Pro Gln Ala Ala Ala Leu Leu
   45                  50                  55 gac ctg gat gaa agc gcg cag atc gcc gcc gtg cag gat ggc ttc gtc      1022
Asp Leu Asp Glu Ser Ala Gln Ile Ala Ala Val Gln Asp Gly Phe Val
60                  65                  70                  75 aac ttc tat gcc gat gat gcg gtg gtg ccc tat atc gcc ctg gcc gcc      1070
Asn Phe Tyr Ala Asp Asp Ala Val Val Pro Tyr Ile Ala Leu Ala Ala
                    80                  85                  90
```

-continued

```
cgc ggg ccg tgg gtg gtc agc ctg aag ggc gcg gtg ctg tat gac gcc    1118
Arg Gly Pro Trp Val Val Ser Leu Lys Gly Ala Val Leu Tyr Asp Ala
             95                 100                 105 ggc ggc tac ggc atg ctc ggc ttc ggc cat acc ccg gcc gat atc ctg    1166
Gly Gly Tyr Gly Met Leu Gly Phe Gly His Thr Pro Ala Asp Ile Leu
        110                 115                 120 gag gcg gtc ggc aag ccg cag gtg atg gcc aac atc atg act ccc tcg    1214
Glu Ala Val Gly Lys Pro Gln Val Met Ala Asn Ile Met Thr Pro Ser
125                 130                 135 ctg gcc cag ggc cgc ttc att gcc gca atg cgc cgc gaa atc ggc cat    1262
Leu Ala Gln Gly Arg Phe Ile Ala Ala Met Arg Arg Glu Ile Gly His
140                 145                 150                 155 acc cgc ggc ggc tgc ccg ttc tcg cac ttc atg tgc ctg aac tcc ggc    1310
Thr Arg Gly Gly Cys Pro Phe Ser His Phe Met Cys Leu Asn Ser Gly
                160                 165                 170 tcc gaa gcg gtc ggg ctg gcc gcg cgc atc gcc gac atc aac gcc aag    1358
Ser Glu Ala Val Gly Leu Ala Ala Arg Ile Ala Asp Ile Asn Ala Lys
            175                 180                 185 ctg atg acc gac ccg ggc gcc cgg cat gcc ggc gcc acg atc aag cgc    1406
Leu Met Thr Asp Pro Gly Ala Arg His Ala Gly Ala Thr Ile Lys Arg
        190                 195                 200 gtg gtg atc aag ggc agt ttc cac ggc cgt acc gac cgt ccg gcg ctg    1454
Val Val Ile Lys Gly Ser Phe His Gly Arg Thr Asp Arg Pro Ala Leu
205                 210                 215 tat tcc gat tcc acc cgc aag gcc tac gat gcg cat ctg gcc agc tac    1502
Tyr Ser Asp Ser Thr Arg Lys Ala Tyr Asp Ala His Leu Ala Ser Tyr
220                 225                 230                 235 cgc gac gag cac agc gtc att gcc atc gcc ccg tat gac cag cag gcc    1550
Arg Asp Glu His Ser Val Ile Ala Ile Ala Pro Tyr Asp Gln Gln Ala
                240                 245                 250 ctg cgc cag gtg ttt gcc gat gcc cag gcc aac cac tgg ttc atc gag    1598
Leu Arg Gln Val Phe Ala Asp Ala Gln Ala Asn His Trp Phe Ile Glu
            255                 260                 265 gcg gtg ttc ctg gag ccg gtg atg ggc gaa ggc gac ccg ggc cgt gcg    1646
Ala Val Phe Leu Glu Pro Val Met Gly Glu Gly Asp Pro Gly Arg Ala
        270                 275                 280 gtg ccg gtg gac ttc tac cgc ctg gcc cgt gag ctg acc cgc gaa cac    1694
Val Pro Val Asp Phe Tyr Arg Leu Ala Arg Glu Leu Thr Arg Glu His
285                 290                 295 ggc agc ctg ctg ctg atc gat tcg atc cag gcc gcg ctg cgc gtg cac    1742
Gly Ser Leu Leu Leu Ile Asp Ser Ile Gln Ala Ala Leu Arg Val His
300                 305                 310                 315 ggc acc ctg tcc ttc gtc gac tac ccc ggc cac cag gag ctg gag gca    1790
Gly Thr Leu Ser Phe Val Asp Tyr Pro Gly His Gln Glu Leu Glu Ala
                320                 325                 330 ccg gac atg gag acc tac tcc aag gcc ctg aac ggc gcc cag ttc ccg    1838
Pro Asp Met Glu Thr Tyr Ser Lys Ala Leu Asn Gly Ala Gln Phe Pro
            335                 340                 345 ctg tcg gta gtg gcc gtg acc gag cac gcc gcc gcg ctg tac cgc aag    1886
Leu Ser Val Val Ala Val Thr Glu His Ala Ala Ala Leu Tyr Arg Lys
        350                 355                 360 ggc gtg tac ggc aac acc atg acc acc aac ccg cgg gcg ctg gac gtg    1934
Gly Val Tyr Gly Asn Thr Met Thr Thr Asn Pro Arg Ala Leu Asp Val
365                 370                 375 gcc tgc gcc acc ctg gca cgc ctg gat gag ccg gtc cgc aac aat atc    1982
Ala Cys Ala Thr Leu Ala Arg Leu Asp Glu Pro Val Arg Asn Asn Ile
380                 385                 390                 395 cgc ctg cgt ggc cag cag gcg atg cag aag ctg gaa gca ttg aag gaa    2030
Arg Leu Arg Gly Gln Gln Ala Met Gln Lys Leu Glu Ala Leu Lys Glu
```

```
                    400            405            410
cgg ctg ggg ggc gcg atc acc aag gtg cag ggc acc ggc ctg ctg ttc        2078
Arg Leu Gly Gly Ala Ile Thr Lys Val Gln Gly Thr Gly Leu Leu Phe
                415                420                425 tcc tgc gag ctg gcc ccg cag tac aag tgc tac ggg gcc ggc tcc acc        2126
Ser Cys Glu Leu Ala Pro Gln Tyr Lys Cys Tyr Gly Ala Gly Ser Thr
            430                435                440 gag gag tgg ctg cgc atg cac ggg gtc aat gtg atc cac ggc ggc gag        2174
Glu Glu Trp Leu Arg Met His Gly Val Asn Val Ile His Gly Gly Glu
        445                450                455 aat tcg ctg cgc ttc acc ccg cac ttc ggc atg gac gag gcc gaa ctg        2222
Asn Ser Leu Arg Phe Thr Pro His Phe Gly Met Asp Glu Ala Glu Leu
460                465                470                475 gac ctg ctg gtg gag atg gtc ggg cgt gcg ctg gtc gaa ggc cca cgc        2270
Asp Leu Leu Val Glu Met Val Gly Arg Ala Leu Val Glu Gly Pro Arg
                480                485                490 cgg gcc tga tccgcacccg caggacggaa ggcacgagcc caccgtgagg cgggctctt     2328
Arg Ala tgctgcccgg caccagcggc aacaggccgc gctgtcaccg gccaggcggg gcgccggcag     2388
tgggtttcag ccgcaggggt ccgccctgcc agcgcctgcg gcggggcaca ggcttgcggg     2448
cattgcggcc tctgccacgg gcacgcagcc ggagatcagg ctgacaaggg ggctgccccg     2508
ggtggcagta cacgaccagc cagttgactg ccggtatttg cttgatcagc gctgcatcca     2568
gaacagcacc atcggttgcg tgactgacgc gccgctggcc gttgcgggac agcagccttt     2628
gcgtcacacg tggcccgcac ctgcctgcac tgcag                                2663

<210> SEQ ID NO 2
<211> LENGTH: 30
<212> TYPE: DNA
<213> ORGANISM: Artificial Sequence
<220> FEATURE:
<223> OTHER INFORMATION: Synthesized to alter a region in the
      neighborhood of the N-terminal ATG of the gene of Flavobacterium
      lutescens encoding lysine 6-aminotransferase (the lat gene) to a
      NdeI site

<400> SEQUENCE: 2
tccatatgtc ccttcttgcc ccgctcgccc                                       30

<210> SEQ ID NO 3
<211> LENGTH: 30
<212> TYPE: DNA
<213> ORGANISM: Artificial Sequence
<220> FEATURE:
<223> OTHER INFORMATION: Synthesized to alter a region downstream of the
      termination codon of the gene of Flavobacterium lutescens encoding
      lysine 6-aminotransferase (the lat gene) to a BamHI site

<400> SEQUENCE: 3
gcggatcctg ttgccgctgg tgccgggcag                                       30

<210> SEQ ID NO 4
<211> LENGTH: 29
<212> TYPE: DNA
<213> ORGANISM: Artificial Sequence
<220> FEATURE:
<223> OTHER INFORMATION: Synthesized to alter a region in the
      neighborhood of the N-terminal ATG of the gene of Flavobacterium
      lutescens encoding lysine 6-aminotransferase (the lat gene) to a
      HindIII site

<400> SEQUENCE: 4
```

```
ataagcttgt cccttcttgc cccgctcgc                                   29
```

<210> SEQ ID NO 5
<211> LENGTH: 1837
<212> TYPE: DNA
<213> ORGANISM: Escherichia coli
<220> FEATURE:

<400> SEQUENCE: 5

```
atttagccac gactacgttg cacttccagc caccacttct ccagctccgc ggcaaaggcc   60
tggcggtcac gttgtgaaag ctatctggt ccgccggtct ggatcccact ggcacgtaag   120
gtatccataa aatcgcgcat cgtcaggcgc tcacgaatgg tcgctggcgt gtaacgttcg   180
ccgcgcggat taagcgccgc agcgcctttc tcgatggctt cagcagccaa aggtatatct   240
gcggtgatca ccaaatcgcc cgcttcacac tgccggacaa tttcgttatc ggcaacgtcg   300
aaacctgccg cgacgcgcag cgtacgaata aatcgcgatg gcggcacgcg taaactctgg   360
tttgctacca gtaccagcgg catctgcata cgttccgccg cgcgatacaa atctctttta   420
attacattgg gacacgcgtc ggcatccacc caaattgtca taaagtcatc ctttgttggg   480
taatcctcta ttgtgtcgcg cttttgcctt ccggcatagt tctgtttatg cttctgccag   540
cgattatcaa acaatgaat ttcacggcag gagtgaggca atg gaa aag aaa atc    595
                                           Met Glu Lys Lys Ile
                                             1               5 ggt ttt att ggc tgc ggc aat atg gga aaa gcc att ctc ggc ggt ctg   643
Gly Phe Ile Gly Cys Gly Asn Met Gly Lys Ala Ile Leu Gly Gly Leu
                10                  15                  20 att gcc agc ggt cag gtg ctt cca ggg caa atc tgg gta tac acc ccc   691
Ile Ala Ser Gly Gln Val Leu Pro Gly Gln Ile Trp Val Tyr Thr Pro
             25                  30                  35 tcc ccg gat aaa gtc gcc gcc ctg cat gac cag ttc ggc atc aac gcc   739
Ser Pro Asp Lys Val Ala Ala Leu His Asp Gln Phe Gly Ile Asn Ala
         40                  45                  50 gca gaa tcg gcg caa gaa gtg gcg caa atc gcc gac atc att ttt gct   787
Ala Glu Ser Ala Gln Glu Val Ala Gln Ile Ala Asp Ile Ile Phe Ala
     55                  60                  65 gcc gtt aaa cct ggc atc atg att aaa gtg ctt agc gaa atc acc tcc   835
Ala Val Lys Pro Gly Ile Met Ile Lys Val Leu Ser Glu Ile Thr Ser
 70                  75                  80                  85 agc ctg aat aaa gac tct ctg gtc gtt tct att gct gca ggt gtc acg   883
Ser Leu Asn Lys Asp Ser Leu Val Val Ser Ile Ala Ala Gly Val Thr
                 90                  95                 100 ctc gac cag ctt gcc cgc gcg ctg ggc cat gac cgg aaa att atc cgc   931
Leu Asp Gln Leu Ala Arg Ala Leu Gly His Asp Arg Lys Ile Ile Arg
            105                 110                 115 gcc atg ccg aac act ccc gca ctg gtt aat gcc ggg atg acc tcc gta   979
Ala Met Pro Asn Thr Pro Ala Leu Val Asn Ala Gly Met Thr Ser Val
        120                 125                 130 acg cca aac gcg ctg gta acc cca gaa gat acc gct gat gtg ctg aat  1027
Thr Pro Asn Ala Leu Val Thr Pro Glu Asp Thr Ala Asp Val Leu Asn
    135                 140                 145 att ttc cgc tgc ttt ggc gaa gcg gaa gta att gct gag ccg atg atc  1075
Ile Phe Arg Cys Phe Gly Glu Ala Glu Val Ile Ala Glu Pro Met Ile
150                 155                 160                 165 cac ccg gtg gtc ggt gtg agc ggt tct tcg cca gcc tac gta ttt atg  1123
His Pro Val Val Gly Val Ser Gly Ser Ser Pro Ala Tyr Val Phe Met
                170                 175                 180 ttt atc gaa gcg atg gcc gac gcc gcc gtg ctg ggc ggg atg cca cgc  1171
Phe Ile Glu Ala Met Ala Asp Ala Ala Val Leu Gly Gly Met Pro Arg
```

```
              185                 190                 195
gcc cag gcg tat aaa ttt gcc gct cag gcg gta atg ggt tcc gca aaa    1219
Ala Gln Ala Tyr Lys Phe Ala Ala Gln Ala Val Met Gly Ser Ala Lys
            200                 205                 210 atg gtg ctg gaa acg gga gaa cat ccg ggg gca ctg aaa gat atg gtc    1267
Met Val Leu Glu Thr Gly Glu His Pro Gly Ala Leu Lys Asp Met Val
        215                 220                 225 tgc tca ccg gga ggc acc acc att gaa gcg gta cgc gta ctg gaa gag    1315
Cys Ser Pro Gly Gly Thr Thr Ile Glu Ala Val Arg Val Leu Glu Glu
230                 235                 240                 245 aaa ggc ttc cgt gct gca gtg atc gaa gcg atg acg aag tgt atg gaa    1363
Lys Gly Phe Arg Ala Ala Val Ile Glu Ala Met Thr Lys Cys Met Glu
                250                 255                 260 aaa tca gaa aaa ctc agc aaa tcc tga tgactttcgc cggacgtcag gccgcca   1417
Lys Ser Glu Lys Leu Ser Lys Ser
                265 cttcggtgcg gttacgtccg gctttctttg ctttgtaaag cgccaaatct gccgatttca   1477 accactcacg atagtgactc atttgtgggt tcagcggcgc aacccccaca ctaatccgta   1537 aagttacctg tggcgtattc ggcaaacgta atgtatttag cccttcatgc acccgtaaca   1597 tggcggtaat ggcgctctca gctggcgtac cggacatgat tactgcaaac tcatcgccgc   1657 caaaccgacc aatcacatcg ctaccgcgca gggtaatttg taactgtcgg gtaagcgcca   1717 caatcgcttc atcgcccaca tcatggcccc aggtatcgtt gatgctcttg aaatggtcga   1777 tatcgataat cagtaacgtt gcatcgcgat tatgccgccg acagttatca aattcattgc   1837
```

<210> SEQ ID NO 6
<211> LENGTH: 30
<212> TYPE: DNA
<213> ORGANISM: Artificial Sequence
<220> FEATURE:
<223> OTHER INFORMATION: Synthesized to alter a region in the
      neighborhood of the N-terminal ATG of the gene of Escherichia coli
      encoding pyrroline-5-carboxylate reductase (the proC gene) to a
      KpnI site

<400> SEQUENCE: 6
agggtaccat aaaatcgcgc atcgtcaggc                                    30

<210> SEQ ID NO 7
<211> LENGTH: 30
<212> TYPE: DNA
<213> ORGANISM: Artificial Sequence
<220> FEATURE:
<223> OTHER INFORMATION: Synthesized to alter a region downstream of the
      termination codon of the proC gene of Escherichia coli to
      a KpnI site

<400> SEQUENCE: 7
ccggtaccgc cacaggtaac tttacggatt                                    30

<210> SEQ ID NO 8
<211> LENGTH: 2186
<212> TYPE: DNA
<213> ORGANISM: Escherichia coli
<220> FEATURE:

<400> SEQUENCE: 8
ggatcctgcg tgaacgcggt tccggcacgc gggagattgt cgattatctg ttgctgtcac    60
atttaccgaa gtttgagatg gcgatggaat taggtaactc cgaggcaatc aaacatgcgg   120
tgcgtcatgg gttgggaatt agttgcctgt cgcgacgtgt gattgaagat caattgcagg   180

```
caggcacatt aagtgaagtt gcggtccctc tgccgcgcct gatgcgtacg ttgtggcgta      240
tacatcatcg gcaaaaacac ctttccaacg cgctacggcg ctttctggac tattgcgatc      300
ccgcaaatgt gccgcgttaa gttgctgtac aagaacatgc tggtgctgtg tcgatttcgt      360
gacgcagcgc cttcagcatg cattcgccag aaaagagatt ggctgcttta cttataatcc      420
ctgggcgatc atgaaggtgt cttataaccg tgtatttctg ccggaaggat tgccaatcgt      480
ctgctacaat cgcgcctcat ttttaagatg gatagcattt ttgt atg gtt tcc gaa      536
                                                  Met Val Ser Glu
                                                   1 act aaa acc aca gaa gcg ccg ggc tta cgc cgt gaa tta aag gcg cgt      584
Thr Lys Thr Thr Glu Ala Pro Gly Leu Arg Arg Glu Leu Lys Ala Arg
  5              10                  15                  20 cac ctg acg atg att gcc att ggc ggt tcc atc ggt aca ggt ctt ttt      632
His Leu Thr Met Ile Ala Ile Gly Gly Ser Ile Gly Thr Gly Leu Phe
             25                  30                  35 gtt gcc tct ggc gca acg att tct cag gca ggt ccg ggc ggg gca ttg      680
Val Ala Ser Gly Ala Thr Ile Ser Gln Ala Gly Pro Gly Gly Ala Leu
         40                  45                  50 ctc tcg tat atg ctg att ggc ctg atg gtt tac ttc ctg atg acc agt      728
Leu Ser Tyr Met Leu Ile Gly Leu Met Val Tyr Phe Leu Met Thr Ser
     55                  60                  65 ctc ggt gaa ctg gct gca tat atg ccg gtt tcc ggt tcg ttt gcc act      776
Leu Gly Glu Leu Ala Ala Tyr Met Pro Val Ser Gly Ser Phe Ala Thr
 70                  75                  80 tac ggt cag aac tat gtt gaa gaa ggc ttt ggc ttc gcg ctg ggc tgg      824
Tyr Gly Gln Asn Tyr Val Glu Glu Gly Phe Gly Phe Ala Leu Gly Trp
 85                  90                  95                 100 aac tac tgg tac aac tgg gcg gtg act atc gcc gtt gac ctg gtt gca      872
Asn Tyr Trp Tyr Asn Trp Ala Val Thr Ile Ala Val Asp Leu Val Ala
                105                 110                 115 gct cag ctg gtc atg agc tgg tgg ttc ccg gat aca ccg ggc tgg atc      920
Ala Gln Leu Val Met Ser Trp Trp Phe Pro Asp Thr Pro Gly Trp Ile
            120                 125                 130 tgg agt gcg ttg ttc ctc ggc gtt atc ttc ctg ctg aac tac atc tca      968
Trp Ser Ala Leu Phe Leu Gly Val Ile Phe Leu Leu Asn Tyr Ile Ser
        135                 140                 145 gtt cgt ggc ttt ggt gaa gcg gaa tac tgg ttc tca ctg atc aaa gtc     1016
Val Arg Gly Phe Gly Glu Ala Glu Tyr Trp Phe Ser Leu Ile Lys Val
    150                 155                 160 acg aca gtt att gtc ttt atc atc gtt ggc gtg ctg atg att atc ggt     1064
Thr Thr Val Ile Val Phe Ile Ile Val Gly Val Leu Met Ile Ile Gly
165                 170                 175                 180 atc ttc aaa ggc gcg cag cct gcg ggc tgg agc aac tgg aca atc ggc     1112
Ile Phe Lys Gly Ala Gln Pro Ala Gly Trp Ser Asn Trp Thr Ile Gly
                185                 190                 195 gaa gcg ccg ttt gct ggt ggt ttt gcg gcg atg atc ggc gta gct atg     1160
Glu Ala Pro Phe Ala Gly Gly Phe Ala Ala Met Ile Gly Val Ala Met
            200                 205                 210 att gtc ggc ttc tct ttc cag gga acc gag ctg atc ggt att gct gca     1208
Ile Val Gly Phe Ser Phe Gln Gly Thr Glu Leu Ile Gly Ile Ala Ala
        215                 220                 225 ggc gag tcc gaa gat ccg gcg aaa aac att cca cgc gcg gta cgt cag     1256
Gly Glu Ser Glu Asp Pro Ala Lys Asn Ile Pro Arg Ala Val Arg Gln
    230                 235                 240 gtg ttc tgg cga atc ctg ttg ttc tat gtg ttc gcg atc ctg att atc     1304
Val Phe Trp Arg Ile Leu Leu Phe Tyr Val Phe Ala Ile Leu Ile Ile
245                 250                 255                 260
```

```
agc ctg att att ccg tac acc gat ccg agc ctg ctg cgt aac gat gtt      1352
Ser Leu Ile Ile Pro Tyr Thr Asp Pro Ser Leu Leu Arg Asn Asp Val
            265                 270                 275 aaa gac atc agc gtt agt ccg ttc acc ctg gtg ttc cag cac gcg ggt      1400
Lys Asp Ile Ser Val Ser Pro Phe Thr Leu Val Phe Gln His Ala Gly
        280                 285                 290 ctg ctc tct gcg gcg gcg gtg atg aac gca gtt att ctg acg gcg gtg      1448
Leu Leu Ser Ala Ala Ala Val Met Asn Ala Val Ile Leu Thr Ala Val
        295                 300                 305 ctg tca gcg ggt aac tcc ggt atg tat gcg tct act cgt atg ctg tac      1496
Leu Ser Ala Gly Asn Ser Gly Met Tyr Ala Ser Thr Arg Met Leu Tyr
    310                 315                 320 acc ctg gcg tgt gac ggt aaa gcg ccg cgc att ttc gct aaa ctg tcg      1544
Thr Leu Ala Cys Asp Gly Lys Ala Pro Arg Ile Phe Ala Lys Leu Ser
325                 330                 335                 340 cgt ggt ggc gtg ccg cgt aat gcc ctg tat gcg acg acg gtg att gcc      1592
Arg Gly Gly Val Pro Arg Asn Ala Leu Tyr Ala Thr Thr Val Ile Ala
                345                 350                 355 ggt ctg tgc ttc ctg acc tcc atg ttt ggc aac cag acg gta tac ctg      1640
Gly Leu Cys Phe Leu Thr Ser Met Phe Gly Asn Gln Thr Val Tyr Leu
        360                 365                 370 tgg ctg ctg aac acc tcc ggg atg acg ggt ttt atc gcc tgg ctg ggg      1688
Trp Leu Leu Asn Thr Ser Gly Met Thr Gly Phe Ile Ala Trp Leu Gly
        375                 380                 385 att gcc att agc cac tat cgc ttc cgt cgc ggt tac gta ttg cag gga      1736
Ile Ala Ile Ser His Tyr Arg Phe Arg Arg Gly Tyr Val Leu Gln Gly
        390                 395                 400 cac gac att aac gat ctg ccg tac cgt tca ggt ttc ttc cca ctg ggg      1784
His Asp Ile Asn Asp Leu Pro Tyr Arg Ser Gly Phe Phe Pro Leu Gly
405                 410                 415                 420 ccg atc ttc gca ttc att ctg tgt ctg att atc act ttg ggc cag aac      1832
Pro Ile Phe Ala Phe Ile Leu Cys Leu Ile Ile Thr Leu Gly Gln Asn
                425                 430                 435 tac gaa gcg ttc ctg aaa gat act att gac tgg ggc ggc gta gcg gca      1880
Tyr Glu Ala Phe Leu Lys Asp Thr Ile Asp Trp Gly Gly Val Ala Ala
            440                 445                 450 acg tat att ggt atc ccg ctg ttc ctg att att tgg ttc ggc tac aag      1928
Thr Tyr Ile Gly Ile Pro Leu Phe Leu Ile Ile Trp Phe Gly Tyr Lys
        455                 460                 465 ctg att aaa gga act cac ttc gta cgc tac agc gaa atg aag ttc ccg      1976
Leu Ile Lys Gly Thr His Phe Val Arg Tyr Ser Glu Met Lys Phe Pro
    470                 475                 480 cag aac gat aag aaa taagtttcct cccttccttg ctaagccctc tcaaccgaga      2031
Gln Asn Asp Lys Lys
485 gggcttttc aattccattt ccctgacaaa tcatgcggat ataaaattta acatttggat     2091
tgataattgt tatcgtttgc attatcgtta cgccgcaatc aaaaaaggct gacaaatcag    2151
aggctgttcc ggctttctgg gatggatcca gatct                               2186

<210> SEQ ID NO 9
<211> LENGTH: 30
<212> TYPE: DNA
<213> ORGANISM: Artificial Sequence
<220> FEATURE:
<223> OTHER INFORMATION: Synthesized to alter a region in the
      neighborhood of the N-terminal ATG of the gene of Escherichia coli
      encoding a lysine-specific permease (lysP) to a BglII site

<400> SEQUENCE: 9
tgagatctgg atcctgcgtg aacgcggttc                                      30
```

-continued

<210> SEQ ID NO 10
<211> LENGTH: 30
<212> TYPE: DNA
<213> ORGANISM: Artificial Sequence
<220> FEATURE:
<223> OTHER INFORMATION: Synthesized to alter a region downstream of the
      termination codon of the lysP gene of Escherichia coli
      to a BamHI site

<400> SEQUENCE: 10

| gcagatctgg atcccagaaa gccggaacag | 30 |
|---|---|

<210> SEQ ID NO 11
<211> LENGTH: 2150
<212> TYPE: DNA
<213> ORGANISM: Escherichia ?oli
<220> FEATURE:

<400> SEQUENCE: 11

| tttgccagac cgccagcagc actaacgtgc gctccaatgt atttcatgcg aggactcctg | 60 |
|---|---|
| ttaaacccgc tggaggaaaa cggtaatgat agcgggttaa caggagcaag atgtagtggt | 120 |
| ttatgcgatg acgctttgaa tcacatagtt aatcgcacca ccaccaacaa tcagccaggc | 180 |
| aaacagtacc agtgccatca gcagaggttt cgccccagct tttttcagcg cgctgacgtg | 240 |
| agtggtcaga cccagcgccg ccatcgccat tgccagcagg aaggtatcca gcgttaccag | 300 |
| catgttcacc acgctctgcg gtaacaggtg gaacgagtta agatggcaa ctacgatgaa | 360 |
| caagatggca aaccacggaa tagtgatttt gcttttctcg ccgctgttcg ccccagacag | 420 |
| ctgtttaaca cgcgccgcca gcaggatgag gaacggagcc agcatcatca cgcgcagcat | 480 |
| tttgaaaata actgctgcgt tttccgcatc cgggctgatg gcatgacctg ccgccaccac | 540 |
| ctgcgccact cgtgcacag tagaaccaat gtagataccg aaagtttccg gactaaacca | 600 |
| ttgagacatc agcggatata tcgccgggta gaggaaaatc gcgacggtcc cgaagataac | 660 |
| aacggttgca acagccacgg ttactttact ggcttccgct ttcactaccg gctcagtcgc | 720 |
| cagtaccgcg gcagcaccac agatactgct accggcaccg atcaaccagc tggtgtgctt | 780 |
| atccagacca aacactttct gccccaggaa gcaagccagc aggaaggtac tggacacgcgt | 840 |
| caacacgtca atgatgatcc cactgatacc gacatcggca atttgcgaga acgtcagacg | 900 |
| gaagccataa agaatgatac ccagacgtaa taaatattgc ttggcaaaca gcacaccacc | 960 |
| gtcacagctt ttccagatgt gcggatagat ggtgttgcct aaaaccatcc ccaacaagat | 1020 |
| tgcgagggtg agggcactaa acccggcacc cgcaaccgcg ggaatggaac cacccacag | 1080 |
| ggcgaccccg gtgataactg cactcagggc taaccccgga ataaaatgcc acagtgtacg | 1140 |
| atgttgtttc tgtaaggtga tattcgtcat aaccctctcc tttaaccggg cataaggtta | 1200 |
| cgactaactg gtttaaaaat aaaattgatt atatatttat aattaatctt tataagtggt | 1260 |
| aagcgact atg cac atc acc ctc cgg cag ttg gaa gtt ttt gca gaa gta | 1310 |
|          Met His Ile Thr Leu Arg Gln Leu Glu Val Phe Ala Glu Val | |
|            1               5                   10                | |
| ttg aaa agt gga tca acc acc cag gcg tcg gtg atg ctg gcg ttg tcg | 1358 |
| Leu Lys Ser Gly Ser Thr Thr Gln Ala Ser Val Met Leu Ala Leu Ser | |
| 15                  20                  25                  30   | |
| caa tca gca gtg agc gca gcc ttg acc gac ctg gaa ggg cag ctt ggc | 1406 |
| Gln Ser Ala Val Ser Ala Ala Leu Thr Asp Leu Glu Gly Gln Leu Gly | |
|             35                  40                  45          | |
| gtg caa ctg ttt gat cgc gtg ggg aaa aga ctg gtt gtt aat gaa cac | 1454 |

```
                Val Gln Leu Phe Asp Arg Val Gly Lys Arg Leu Val Val Asn Glu His
                             50                  55                  60 gtg cgg ctg ctc tat ccg cgt gcg ttg gca ttg ctt gaa cag gcg gtt      1502
Gly Arg Leu Leu Tyr Pro Arg Ala Leu Ala Leu Leu Glu Gln Ala Val
         65                  70                  75 gaa atc gaa caa ctg ttt cgc gaa gac aac ggc gcg att cgt atc tat      1550
Glu Ile Glu Gln Leu Phe Arg Glu Asp Asn Gly Ala Ile Arg Ile Tyr
 80                  85                  90 gcc agt agt acc atc ggt aac tac att ctg cct gca gtt atc gcc cgt      1598
Ala Ser Ser Thr Ile Gly Asn Tyr Ile Leu Pro Ala Val Ile Ala Arg
 95                 100                 105                 110 tat cgc cat gat tat ccg cag ttg ccg att gaa ctt agc gtt ggg aat      1646
Tyr Arg His Asp Tyr Pro Gln Leu Pro Ile Glu Leu Ser Val Gly Asn
                115                 120                 125 agc cag gac gtg atg caa gcg gtg ctg gat ttc cgc gtt gat att ggc      1694
Ser Gln Asp Val Met Gln Ala Val Leu Asp Phe Arg Val Asp Ile Gly
            130                 135                 140 ttt att gaa gga ccg tgc cac agc act gaa atc att tct gaa ccg tgg      1742
Phe Ile Glu Gly Pro Cys His Ser Thr Glu Ile Ile Ser Glu Pro Trp
145                 150                 155 ctg gaa gac gag ctg gtg gtt ttc gcc gcg ccg act tcg ccg ttg gcc      1790
Leu Glu Asp Glu Leu Val Val Phe Ala Ala Pro Thr Ser Pro Leu Ala
        160                 165                 170 cgt ggt ccg gtc acc tta gaa cag ctg gcc gct gcg ccg tgg atc ctg      1838
Arg Gly Pro Val Thr Leu Glu Gln Leu Ala Ala Ala Pro Trp Ile Leu
175                 180                 185                 190 cgt gaa cgc ggt tcc ggc acg cgg gag att gtc gat tat ctg ttg ctg      1886
Arg Glu Arg Gly Ser Gly Thr Arg Glu Ile Val Asp Tyr Leu Leu Leu
                195                 200                 205 tca cat tta ccg aag ttt gag atg gcg atg gaa tta ggt aac tcc gag      1934
Ser His Leu Pro Lys Phe Glu Met Ala Met Glu Leu Gly Asn Ser Glu
            210                 215                 220 gca atc aaa cat gcg gtg cgt cat ggg ttg gga att agt tgc ctg tcg      1982
Ala Ile Lys His Ala Val Arg His Gly Leu Gly Ile Ser Cys Leu Ser
        225                 230                 235 cga cgt gtg att gaa gat caa ttg cag gca ggc aca tta agt gaa gtt      2030
Arg Arg Val Ile Glu Asp Gln Leu Gln Ala Gly Thr Leu Ser Glu Val
240                 245                 250 gcg gtc cct ctg ccg cgc ctg atg cgt acg ttg tgg cgt ata cat cat      2078
Ala Val Pro Leu Pro Arg Leu Met Arg Thr Leu Trp Arg Ile His His
255                 260                 265                 270 cgg caa aaa cac ctt tcc aac gcg cta cgg cgc ttt ctg gac tat tgc      2126
Arg Gln Lys His Leu Ser Asn Ala Leu Arg Arg Phe Leu Asp Tyr Cys
                275                 280                 285 gat ccc gca aat gtg ccg cgt taa                                      2150
Asp Pro Ala Asn Val Pro Arg
            290

<210> SEQ ID NO 12
<211> LENGTH: 32
<212> TYPE: DNA
<213> ORGANISM: Artificial Sequence
<220> FEATURE:
<223> OTHER INFORMATION: Synthesized to attach a BglII site to a
      position in the neighborhood of the 5'-terminus of the lysP type
      transcriptional  regular yeiE of Escherichia coli

<400> SEQUENCE: 12
atagatctct tgttgcctaa aaccatcccc aa                                    32

<210> SEQ ID NO 13
```

```
<211> LENGTH: 31
<212> TYPE: DNA
<213> ORGANISM: Artificial Sequence
<220> FEATURE:
<223> OTHER INFORMATION: Synthesized to attach a KpnI site to a position
      downstream of the termination codon of the lysP gene of
      Escherichia coli

<400> SEQUENCE: 13
gtggtacccc ccagaaagcc ggaacagcct c                              31

<210> SEQ ID NO 14
<211> LENGTH: 27
<212> TYPE: DNA
<213> ORGANISM: Artificial Sequence
<220> FEATURE:
<223> OTHER INFORMATION: Synthesized

<400> SEQUENCE: 14
tcggtacctc gacattttgt ttctgcc                                   27

<210> SEQ ID NO 15
<211> LENGTH: 27
<212> TYPE: DNA
<213> ORGANISM: Artificial Sequence
<220> FEATURE:
<223> OTHER INFORMATION: Synthesized

<400> SEQUENCE: 15
atggtaccat aaaattgacc atcaagg                                   27

<210> SEQ ID NO 16
<211> LENGTH: 30
<212> TYPE: DNA
<213> ORGANISM: Artificial Sequence
<220> FEATURE:
<223> OTHER INFORMATION: Synthesized

<400> SEQUENCE: 16
ttagtactct tatcatcgat aagctttaat                                30

<210> SEQ ID NO 17
<211> LENGTH: 30
<212> TYPE: DNA
<213> ORGANISM: Artificial Sequence
<220> FEATURE:
<223> OTHER INFORMATION: Synthesized

<400> SEQUENCE: 17
gcagtactac agttctccgc aagaattgat                                30

<210> SEQ ID NO 18
<211> LENGTH: 1295
<212> TYPE: DNA
<213> ORGANISM: Escherichia coli
<220> FEATURE:

<400> SEQUENCE: 18
cgatcaaatc ctcgacattt tgtttctgcc attcaatcga acgctgcga ttcaaccgct    60 atacctgcta tcttcaactt caggacaata atgcaacgtc ttattaacat atttaacgtt  120
gaatgttact gttgtcgtca agatggcata agacctgcat gaaagagcct gcaaacacac  180
aacacaatac acaacataaa aaagccattt tcacttgagg gttatgt atg aag aag    236
                                                     Met Lys Lys
                                                      1
```

```
tcg att ctc gct ctg tct ttg tta gtc ggt ctc tcc aca gcg gct tcc      284
Ser Ile Leu Ala Leu Ser Leu Leu Val Gly Leu Ser Thr Ala Ala Ser
      5                  10                  15 agc tat gcg gcg cta ccg gag acg gta cgt atc gga acc gat acc acc      332
Ser Tyr Ala Ala Leu Pro Glu Thr Val Arg Ile Gly Thr Asp Thr Thr
 20                  25                  30                  35 tac gca ccg ttc tca tcg aaa gat gct aaa ggt gat ttt gtt ggc ttt      380
Tyr Ala Pro Phe Ser Ser Lys Asp Ala Lys Gly Asp Phe Val Gly Phe
                 40                  45                  50 gat atc gat ctc ggt aac gag atg tgc aaa cgg atg cag gtg aaa tgt      428
Asp Ile Asp Leu Gly Asn Glu Met Cys Lys Arg Met Gln Val Lys Cys
                     55                  60                  65 acc tgg gtt gcc agt gac ttt gac gcg ctg atc ccc tca ctg aaa gcg      476
Thr Trp Val Ala Ser Asp Phe Asp Ala Leu Ile Pro Ser Leu Lys Ala
             70                  75                  80 aaa aaa atc gac gct att att tcg tcg ctt tcc att acc gat aaa cgt      524
Lys Lys Ile Asp Ala Ile Ile Ser Ser Leu Ser Ile Thr Asp Lys Arg
         85                  90                  95 cag cag gag att gcc ttc tcc gac aag ctg tac gcc gca gat tct cgt      572
Gln Gln Glu Ile Ala Phe Ser Asp Lys Leu Tyr Ala Ala Asp Ser Arg
100                 105                 110                 115 ttg att gcg gcc aaa ggt tca ccg att cag cca acg ctg gat tca ctg      620
Leu Ile Ala Ala Lys Gly Ser Pro Ile Gln Pro Thr Leu Asp Ser Leu
                 120                 125                 130 aaa ggt aaa cat gtt ggt gtg ctg cag gga tca acc cag gaa gct tac      668
Lys Gly Lys His Val Gly Val Leu Gln Gly Ser Thr Gln Glu Ala Tyr
                     135                 140                 145 gct aac gag acc tgg cgt agt aaa ggc gtg gat gtg gtg gcc tat gcc      716
Ala Asn Glu Thr Trp Arg Ser Lys Gly Val Asp Val Val Ala Tyr Ala
             150                 155                 160 aac cag gat ttg gtc tat tcc gat ctg gct gca gga cgt ctg gat gct      764
Asn Gln Asp Leu Val Tyr Ser Asp Leu Ala Ala Gly Arg Leu Asp Ala
         165                 170                 175 gcg tta caa gat gaa gtt gct gcc agc gaa gga ttc ctc aag caa cct      812
Ala Leu Gln Asp Glu Val Ala Ala Ser Glu Gly Phe Leu Lys Gln Pro
180                 185                 190                 195 gct ggt aaa gat ttc gcc ttt gct ggc tca tca gta aaa gac aaa aaa      860
Ala Gly Lys Asp Phe Ala Phe Ala Gly Ser Ser Val Lys Asp Lys Lys
                 200                 205                 210 tac ttc ggt gat ggc acc ggt gta ggg cta cgt aaa gat gat gct gaa      908
Tyr Phe Gly Asp Gly Thr Gly Val Gly Leu Arg Lys Asp Asp Ala Glu
                     215                 220                 225 ctg acg gct gcc ttc aat aag gcg ctt ggc gag ctg cgt cag gac ggc      956
Leu Thr Ala Ala Phe Asn Lys Ala Leu Gly Glu Leu Arg Gln Asp Gly
             230                 235                 240 acc tac gac aag atg gcg aaa aag tat ttc gac ttt aat gtc tac ggt     1004
Thr Tyr Asp Lys Met Ala Lys Lys Tyr Phe Asp Phe Asn Val Tyr Gly
245                 250                 255 gac tgatacgtcg ctgggaagct gtacctgatg gaatgatcat catggtgc            1055
Asp
260 acgccaggtt tgttgcacta tcgtggtgca ttgaaatgca tacttaagca tttttaatga   1115 aaaataatac gtctaacggg gcgggatatt ttgccttgat ggtcaatttt atggcacgat   1175 aagtgtaaca aacctgtaaa tattccctat aaaaagactg tcagttgagg acattatgaa   1235 aaaactggtg ctatcgctct ctctggttct ggccttctcc agcgcaactg cggcgtttgc   1295
```

<210> SEQ ID NO 19
<211> LENGTH: 29

```
-continued

<212> TYPE: DNA
<213> ORGANISM: Artificial Sequence
<220> FEATURE:
<223> OTHER INFORMATION: Synthesized

<400> SEQUENCE: 19
ggggtaccca tgtcccttct tgccccgct                                29

<210> SEQ ID NO 20
<211> LENGTH: 28
<212> TYPE: DNA
<213> ORGANISM: Artificial Sequence
<220> FEATURE:
<223> OTHER INFORMATION: Synthesized

<400> SEQUENCE: 20
ggggatcccg cggcctgttg ccgctggt                                 28
```

This invention claimed is:

1. A process for the production of L-pipecolic acid which comprises the step of reducing delta-1-piperideine-6-carboxylic acid by the use of pyrroline-5-carboxylate reductase, wherein the delta-1-piperideine-6-carboxylic acid is obtained by the step of converting L-lysine by the use of lysine 6-aminotransferase encoded by a gene of *Flavobacterium lutescens*.

2. The process as claimed in claim 1 wherein the pyrroline-5-carboxylate reductase is encoded by a gene of *Escherichia coli* or a coryneform bacterium.

3. The process as claimed in claim 1 wherein the step of reducing delta-1-piperideine-6-carboxylic acid and the step of converting L-lysine into L-pipecolic acid by the use of lysine 6-aminotransferase are carried out by using a bacterium transformed with a gene encoding lysine 6-aminotransferase wherein such bacterium comprises pyrroline-5-carboxylate reductase.

* * * * *